United States Patent
Drenthen et al.

(10) Patent No.: US 10,359,410 B2
(45) Date of Patent: Jul. 23, 2019

(54) MEASURING ROD FOR VERIFICATION OF A FLOWING MEDIUM IN A TUBE AND RESPECTIVE MEASURING ARRANGEMENTS

(71) Applicant: KROHNE Messtechnik GmbH, Duisburg (DE)

(72) Inventors: Jan Drenthen, Oosterbout (NL); Michael Deilmann, Essen (DE); Michael Vogt, Bochum (DE); Thomas Musch, Bochum (DE); Stephan Neuburger, Stadecken-Elsheim (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 250 days.

(21) Appl. No.: 15/443,082

(22) Filed: Feb. 27, 2017

(65) Prior Publication Data
US 2017/0248570 A1     Aug. 31, 2017

(30) Foreign Application Priority Data
Feb. 26, 2016   (DE) ........................ 10 2016 103 419

(51) Int. Cl.
*G01N 33/28*      (2006.01)
*G01F 1/64*       (2006.01)
(Continued)

(52) U.S. Cl.
CPC ........... *G01N 33/2841* (2013.01); *G01F 1/32* (2013.01); *G01F 1/64* (2013.01); *G01F 1/667* (2013.01);
(Continued)

(58) Field of Classification Search
None
See application file for complete search history.

(56) References Cited

U.S. PATENT DOCUMENTS 3,722,273 A * 3/1973 Yamasaki ............. G01F 1/3218
                                              73/861.22
3,935,484 A * 1/1976 Leschek ................ B06B 1/0685
                                              310/327
(Continued)

FOREIGN PATENT DOCUMENTS

DE    20 2005 009 609 U1   11/2006
DE    10 2006 023 478 A1   11/2007
(Continued)

*Primary Examiner* — Paul M. West
*Assistant Examiner* — Mark A Shabman
(74) *Attorney, Agent, or Firm* — David S. Safran; Roberts Mlotkoski Safran Cole & Calderon, P.C.

(57) ABSTRACT

A measuring rod (1) with a longitudinal axis (A) for insertion in the flow cross section of a tube and for the verification of a flowing medium in this tube having at least one first sender unit (2) for the transmission of a first acoustic or electromagnetic measuring signal (3) and at least one first receiver unit (4) for receiving the first measuring signal, wherein the first sender unit (2) and the first receiver unit (4) define a measuring section, wherein the first sender unit (2) is arranged in such a manner that the first measuring signal (3) crosses the measuring section and wherein the first receiver unit (4) is arranged in such a manner that it, at least during operation without flow, receives the first measuring signal (3) after crossing the measuring section.

17 Claims, 6 Drawing Sheets

(51) Int. Cl.
*G01F 1/66* (2006.01)
*G01F 1/708* (2006.01)
*G01F 1/712* (2006.01)
*G01N 22/00* (2006.01)
*G01N 29/024* (2006.01)
*G01N 29/50* (2006.01)
*G01F 1/32* (2006.01)

(52) U.S. Cl.
CPC ............ *G01F 1/708* (2013.01); *G01F 1/7082* (2013.01); *G01F 1/7088* (2013.01); *G01F 1/712* (2013.01); *G01N 22/00* (2013.01); *G01N 29/024* (2013.01); *G01N 29/50* (2013.01); *G01N 33/2823* (2013.01); *G01N 2291/011* (2013.01); *G01N 2291/02433* (2013.01)

(56) References Cited

U.S. PATENT DOCUMENTS

| | | | | |
|---|---|---|---|---|
| 4,257,277 A | * | 3/1981 | Klobe | G01F 1/3254 73/861.24 |
| 4,708,021 A | * | 11/1987 | Braun | G01P 5/18 702/45 |
| 4,977,781 A | * | 12/1990 | Misumi | G01F 1/3218 73/861.22 |
| 6,351,999 B1 | * | 3/2002 | Maul | G01F 1/3209 356/439 |
| 7,336,160 B2 | | 2/2008 | Niemann | |
| 7,870,793 B1 | * | 1/2011 | Feller | G01F 1/667 73/861.27 |
| 8,958,068 B2 | | 2/2015 | Baer | |
| 2004/0011141 A1 | * | 1/2004 | Lynnworth | G01F 1/662 73/861.27 |
| 2009/0007625 A1 | * | 1/2009 | Ao | G01F 1/668 73/1.31 |
| 2015/0308869 A1 | * | 10/2015 | Black | G01N 29/036 73/861.04 |
| 2016/0313158 A1 | | 10/2016 | Ueberschlag et al. | |

FOREIGN PATENT DOCUMENTS

| | | |
|---|---|---|
| EP | 0 477 419 A1 | 4/1992 |
| EP | 2 103 911 B1 | 9/2014 |

\* cited by examiner

MEASURING ROD FOR VERIFICATION OF A FLOWING MEDIUM IN A TUBE AND RESPECTIVE MEASURING ARRANGEMENTS

BACKGROUND OF THE INVENTION

Field of the Invention

The present invention relates to a measuring rod having a longitudinal axis for insertion in the flow cross section of a tube and for verification of a flowing medium in this tube and a measuring arrangement provided therefore.

Description of the Related Art

In particular, the invention relates to a measuring rod and a measuring arrangement for the verification of a quickly flowing medium such as flare gas. Flare gases are exhaust gases that arise in the extraction of crude oil, in refineries as well as in chemical factories. They contain volatile organic compounds (VOCs), sulfur dioxide, methane and/or further gases that are harmful for health or the environment. Flare gases are burned before they are able to reach the environment in an untreated state. The environmental impact of these gases is reduced by burning. For this, the flare gas is guided through pressure control valves and safety valves into a flare stack with a flame burning at its exit.

In this respect, it is of particular interest for the crude oil and chemical industries to verify the presence of flare gases in pipelines in order, for example, to proceed with the burning of the gases in a controlled manner.

The flare gas reaches the flare stack under high pressure, so that it has a flow speed of up to 200 m/s. This speed, as well as the high degree of contamination of the gas, make for stringent requirements in the methods for the verification of flare gases.

It is known from the prior art to detect at least partially gaseous media using the interaction of this media with ultrasound signals.

A known measurement method is the transit time difference method. It is thereby exploited that ultrasound signals transmitted in the direction of movement of a flowing medium are transmitted faster than ultrasound signals that move opposite the direction of movement. The flow speed of the gas to be to be examined can be calculated from the transit time difference of two signals that cover the same path, wherein one ultrasound signal is transmitted in the direction of flow and one is transmitted in the opposite direction. Respective transit time difference measurements using ultrasound signals are suitable for flow speeds in the range of up to 40 m/s.

The German Patent DE 3504622 C1 and corresponding U.S. Pat. No. 4,708,021 disclose a device for measuring the speed of a flowing medium, wherein two sensors are arranged offset to one another on a pipeline and wherein the sensors temporally detect an inhomogeneity of the medium successively. The speed of the medium is determined from the cross correlation of the two measuring signals.

Additionally, it is known to characterize gases, in particular multi-phase gases, by the interaction with electromagnetic waves, preferably with microwaves. Known methods thereby detect a change in the amplitude and the phase of microwave signals after crossing through the medium. This effect is based on the medium having a permittivity different than that of air, in particular due to the solid and/or liquid particles, whereby the magnitude, amplitudes and phases of the microwave signal dependent on the permittivity are changed by the interaction with the medium. In particular in pipelines with large nominal diameters, the verification using microwave signals, however, proves to be difficult, since interfering reflections superimpose the measured signal and make verification more difficult.

The German Patent Application DE 10 211 102 991 A1 and corresponding U.S. Pat. No. 8,958,068 B2 disclose a device for determining the volume portion of a component of a multi-phase medium based on the transit time of an electromagnetic signal through the medium. The effect is thereby exploited that the propagation speed of the electromagnetic signal is material dependent. In order to make the relevant wanted signal distinguishable from interference signals that are not of interest, the wanted signal is characterized in view of its polarization.

SUMMARY OF THE INVENTION

A primary object of the present invention, based on the above-described prior art, is to provide a device as well as a measuring arrangement for the verification of a quickly flowing medium that can be used particularly flexibly.

This object is achieved according to a first teaching of the invention by a measuring rod as described in the introduction in that the measuring rod comprises at least one first sender unit for the transmission of a first acoustic or electromagnetic measuring signal and at least a first receiver unit for receiving the first measuring signal, wherein the first sender unit and the first receiver unit define a measuring section and wherein the first sender unit is arranged so that the first measuring signal crosses the measuring section and wherein the first receiver unit is arranged so that it, at least during operation without flow, receives the first measuring signal after crossing the measuring section.

The measuring rod according to the invention provides a device for the verification of a quickly flowing medium, wherein the interaction of the medium with an acoustic or electromagnetic signal is the basis for the verification of the medium. In order to provide ideal conditions for this verification, a measuring section is defined by the measuring rod, in detail by the arrangement of the sender unit and the receiver unit. The measuring rod is thereby designed in such a manner that the medium to be verified flows through the measuring section during operation and interacts with the measuring signal within the measuring section. In this respect, a defined measuring section is given, in particular when the measuring rod is inserted in tubes with large nominal diameters, the measuring section being preferably designed in such a manner that interfering reflections superimposing the measuring signal are avoided as far as possible. The measuring rod according to the invention can, thus, be particularly flexibly used. One advantage of the measuring section being implemented with the measuring rod in one unit is that the measuring section can be very easily installed in a provided tube, since the measuring rod is quasi simply inserted in the flow cross section from the outside into the respective tube and has to be attached there. The implementation of the measuring section on or in the measuring rod ensures that the measuring section can be manufactured practically with all possibilities and the precision of modern industrial production technology, the quality of the construction of the measuring section is not dependent on the industrial environment and installation conditions of the future installation site.

Fundamentally, the first sender unit and the first receiver unit can be arranged opposite one another, alternatively, however, they can also be arranged on the same side of the measuring rod, in particular, the sender unit can be designed in such a manner that it can be simultaneously used as a receiver unit.

The verification of the quickly flowing medium is carried out on the basis of the interaction of the medium to be verified with the first measuring signal within the measuring section. For example, the interaction of a medium with the electromagnetic measuring signal, for example with a radar or microwave signal, causes a phase shift and a damping of the amplitude of the measuring signal due to the permittivity of the medium being different than that of air. Alternatively, if the measuring signal is designed as an acoustic signal, in particular an ultrasound signal, a quickly flowing medium can be verified in that the first receiver unit receives an ultrasound signal during operation without flow, whereas in the presence of a quickly flowing medium, the measuring signal does not reach the receiver unit due to the high speed of the medium as well as the coupling of the ultrasound signal to the medium as carrier. The measuring signal detected by the receiver unit, in this respect, is interrupted by the presence of a quickly flowing medium.

Preferably, at least one further receiver unit is provided, which is arranged behind the first receiver unit in respect to flow direction, and which is designed and arranged in such a manner that it receives a measuring signal as long as the measuring signal is designed as an ultrasound signal and as long as a quickly flowing medium is present within the measuring section.

According to a further preferred design of the measuring rod according to the invention, the first sender unit and the first receiver unit are spaced at a distance to one another in respect to the longitudinal axis. The measuring section defined by the sender unit and the receiver unit is then particularly simply designed. In particular, the occurrence of interfering reflections is prevented. A measuring section that is as long as possible is defined by this arrangement.

Preferably, an electric contact of the first sender unit and the first receiver unit runs within the measuring rod. The measuring rod has a particularly simple handling due to the contact integrated in the rod, in particular in respect to the insertion in a tube, free guidance of cables in the—often harsh—technical process is prevented.

In a preferred design, further sensors are integrated in the measuring rod itself, in particular such sensors that do not have to come in direct contact with the exterior of the measuring rod. These are, for example, acceleration sensors with which even small forces and vibrations of the measuring rod caused by them can be detected.

According to a further design of the measuring rod according to the invention, the sender unit and the receiver unit are placed on the circumference of the measuring rod. The construction, as well as the manufacturing of a measuring rod designed in this manner, are particularly easy.

As an alternative to the above-described design, it is also advantageous when the measuring rod has a recess extending along its longitudinal axis, wherein at least one longitudinal surface and two end faces are formed by the recess in the measuring rod and the measuring section is formed in the recess between the two end faces. The first longitudinal surface is preferably thereby designed flat. It preferably runs essentially parallel to the longitudinal axis, i.e. the normal vector is essentially perpendicular on the longitudinal axis. The end faces are preferably arranged essentially perpendicular to the longitudinal axis, i.e. the normal vector of the end faces runs parallel to the longitudinal axis. Such a design of the measuring rod according to the invention has the advantage that the flow to be verified is positively influenced in view of flow rectification in the area of the measuring section due to the flat longitudinal surface, which has an advantageous effect on the verification of the medium, as is described in more detail below.

According to a further design, a second longitudinal surface is formed by the recess in the measuring rod, wherein the first longitudinal surface and the second longitudinal surface meet at a longitudinal edge and form an angle. The second longitudinal surface is thereby, during operation, arranged before the measuring section in respect to flow direction. If the measuring rod has the medium to be verified flowing around it, the second longitudinal surface creates a vortex signature, which, due to the interaction, can be detected with the measuring signal, as is described in detail in the following.

It is further preferred, when a third longitudinal surface is additionally formed by the recess in the measuring rod, in particular wherein the first longitudinal surface, the second longitudinal surface and the third longitudinal surface form a groove in the measuring rod. In this variation, the first sender and the first receiver are particularly protectively sheltered.

It is particularly preferred when at least one flow rectifier is provided for generating a rectified flow of the medium to be verified in the area of the measuring section. A rectified flow is advantageous for the verification of a flowing medium in that fluctuations of the measured effect due to chance turbulence of the flow to be verified are prevented as much as possible.

According to a further preferred design, the flow rectifier is designed in the form of at least two wing-like profile bodies, wherein the wing-like profile bodies are arranged at least in the area of the measuring section. Wing-like profile bodies are streamlined and generate a particularly even flow. Additionally or alternatively, the flow rectifier can also be designed in the form of a grate that is arranged before the measuring section in respect to flow direction.

According to another preferred design of the measuring rod according to the invention, at least one bluff body is provided, wherein the bluff body is arranged before the measuring section in respect to flow direction. A specific marking of the flowing medium can take place using a bluff body, which can be used advantageously for its verification. In detail, vortices are formed behind the bluff bodies within the measuring section that can be detected by means of the measuring signal. In particular, the combination of a flow rectifier with a bluff body thereby generates a vortex signature, which makes a particularly certain verification of the flowing medium possible. It is particularly advantageous when the bluff body is arranged in the area of the rectified flow during operation. Then, the vortex signature is superimposed by a rectified flow, so that the vortex signature created by the bluff body is particularly pronounced. The bluff body is preferably formed as a triangle, however can have another form, for example a rectangle shape.

In a further design, the bluff body is designed as an active bluff body, in the sense that the bluff body can carry out active movements in order to impress the medium flowing by specifically with a certain vortex signature.

The verification of the vortex signature is based on the effect that pressure fluctuations are present within the vortex, which affect the permittivity and, in this respect, cause, for example, a phase change of the electromagnetic measuring signal. Accordingly, the effect of the interaction between the medium and the measuring signal is clearly intensified by the presence of a vortex signature.

Additionally, the vortex signature can also be detected by means of acoustic ultrasound signals, since the pressure or speed fluctuations prevailing within the vortex change the phasing of the acoustic measuring signal, so that, as a result, a phase-modulated measuring signal is created.

According to a further preferred implementation, at least one pressure sensor, preferably a piezo transducer is provided, which is arranged within the measuring section or after it in respect to flow direction. The piezo transducer is, in any case, subject to the exterior of the measuring rod, i.e. also to the flowing medium to be detected, when the measuring rod is mounted for use in a tube. The pressure sensor measures the pressure or possibly occurring pressure differences during operation, which, in particular, are present when the medium to be verified has a vortex signature in the area of the measuring section. If a bluff body is additionally present, then it is also preferred when a pressure sensor is additionally or alternatively arranged in the bluff body.

Preferably, a protective ring is arranged between the tube-side end and the measuring section, wherein the protective ring annularly encompasses the circumference of the measuring rod and wherein the protective ring prevents a transgression of liquid from the tube-side end of the measuring section. If a medium is verified with the help of the measuring rod according to the invention, the protective ring protects the measuring section during operation from liquid running off on the inner walls of the tube.

According to a further preferred design of the measuring rod according to the invention, at least one ceramic window is arranged in the area of the recess for coupling at least the first measuring signal in. According to this design, the coupling of the measuring signal into the measuring section is particularly efficient. It is particularly preferred to arrange the ceramic window directly before the first sender unit.

Preferably, a further ceramic window is provided for coupling the first measuring signal out, wherein the second ceramic window is arranged directly before the receiver unit. The transmission of the measuring signal to the receiver unit is particularly efficient according to this design.

Furthermore, it is also preferred, when, in the area of the recess, the measuring rod has at least one reflector that is arranged in such a manner that at least the first measuring signal is reflected toward the receiver unit after crossing through the measuring section. Preferably, the first sender unit and the first receiver unit are arranged on the same side of the measuring section in this arrangement. It is particularly preferred that the first sender unit is designed in such a manner that it is used simultaneously as first receiver unit. The arrangement has the advantage that the interaction section between the medium to be verified and the measuring signal is made longer, so that the effect to be verified is also intensified.

This design can be further improved in that the measuring section forms a resonator for the measuring signal. If a resonator mode is excited by means of the measuring signal, which particularly is preferably provided in the form of a microwave according to this design, the interaction section between the medium to be verified and the measuring signal is multiply increased, whereby the effect to be verified can be significantly intensified.

According to a next design of the measuring rod according to the invention, at least one second sender unit is provided for transmission of a second acoustic or electromagnetic measuring signal and at least one second receiver unit is provided for receiving the second measuring signal, wherein the second sender unit is arranged in such a manner that the second measuring signal crosses the measuring section, wherein the second receiver unit is arranged in such a manner that it, at least during operation without flow, receives the second measuring signal after crossing the measuring section and wherein the second sender unit and the second receiver unit are arranged behind the first sender unit in respect to flow direction and behind the first receiver unit in respect to flow direction. The medium can be measured in an advantageous manner at two positions according to this design. If a marking, for example in the form of a vortex, is used in the flow during operation, then, in addition to the verification of the presence of the flowing medium, information about the transit time of respective markings, and in this respect, about the speed of the medium can also be obtained using the cross correlation method.

According to one design of the measuring rod according to the invention, at least one evaluation unit is provided, which is connected at least to the first receiver unit and/or the second receiver unit. During operation, the first receiver unit and/or the second receiver unit forward the received measuring signal to the evaluation unit, which then evaluates the measuring signal in view of the interaction parameter. The evaluation unit determines the amplitude and/or the phase and/or the intensity and/or the transit time of the measuring signal and/or the cross correlation of the first and the second measuring signals. The evaluation unit supplies, in any case, a measured value obtained from the first and/or the second measuring signal.

Preferably, a transmitting device is integrated in the measuring rod, which encodes the measured value into a suitable electric signal and transmits it outside of the measuring rod, for example, via an electric contact device. The encoding can take place according to one or according to several interface standards. In one design, the measuring rod is designed as a two-wire device with a 4 mA to 20 mA interface. In a further design, additionally or alternatively, a digital transmission protocol is provided, for example in the form of a HART interface.

According to a second teaching of the invention, the object described in the introduction is achieved by a measuring arrangement comprising a tube and a measuring rod according to one of the above designs, wherein the measuring rod is arranged at least partially within the tube. The measuring arrangement according to the invention has the advantage that a defined measuring section is provided regardless of the nominal diameter of the tube, which provides ideal conditions for the verification of the medium. Influencing the verification, for example due to interfering reflections, can be prevented using the measuring arrangement according to the invention.

According to a preferred design of the measuring arrangement according to the invention, the tube has a radius, wherein the measuring rod extends into the tube at no more than half of the radius, preferably at no more than one third of the radius.

A measuring arrangement according to the invention is particularly preferred when a bluff body is provided, wherein the bluff body is arranged before the measuring rod in respect to the flow direction. In particular when, at the same time, a flow rectifier is provided, a particularly certain verification of the flowing medium can take place.

In detail, there is a plurality of possibilities for designing the measuring rod according to the invention and the measuring arrangement according to the invention as will be apparent from the following description of preferred embodiments in conjunction with the accompanying drawings.

DETAILED DESCRIPTION OF THE INVENTION

Figure 1:
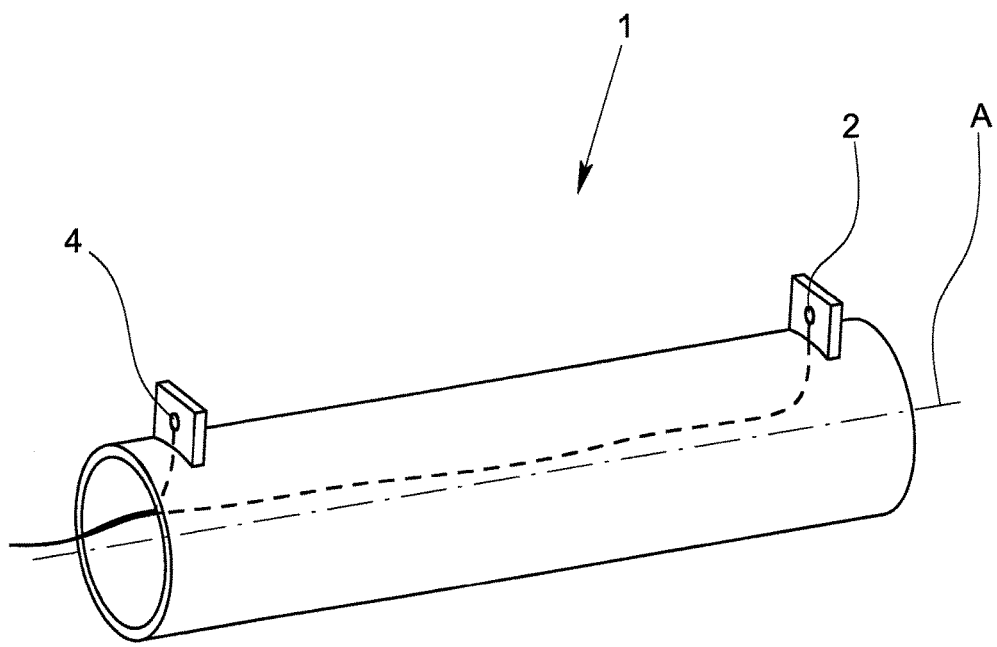
FIG. 1 is a perspective view of a first embodiment of a measuring rod according to the invention with a mounted sender unit and receiver unit.

A first embodiment of a measuring rod 1 according to the invention having a longitudinal axis A for insertion in the flow cross section of a tube and for verification of a flowing medium in this tube is shown in a three-dimensional view in FIG. 1. The measuring rod 1 has a first sender unit 2 for transmission of a first acoustic or electromagnetic measuring signal and a first receiver unit 4 for receiving the first measuring signal 3, wherein the first sender unit 2 and the first receiver unit 4 are arranged at a distance from one another in respect to the longitudinal axis A. The sender unit 2 and the receiver unit 4 define a measuring section, which has the medium to be verified flowing through it during operation. The first sender unit 2 is thereby arranged in such a manner that the first measuring signal crosses the measuring section and the first receiver unit 4 is arranged in such a manner that it, at least during operation without flow, receives the first signal after crossing the measuring section. In the embodiment shown, the sender unit 2 and the receiver unit 4 are placed on the circumference of the measuring rod 1. Additionally, an electric contact of the sender unit 2 and the receiver unit 4 is provided, which runs within the measuring rod 1.

The illustrated first embodiment, in this respect, shows a measuring rod 1 for the verification of a flowing medium in a tube, which is particularly easy to handle and manufacture due to its design and which is particularly flexible, in particular can be used in combination with tubes having a large nominal diameter.

Figure 2:
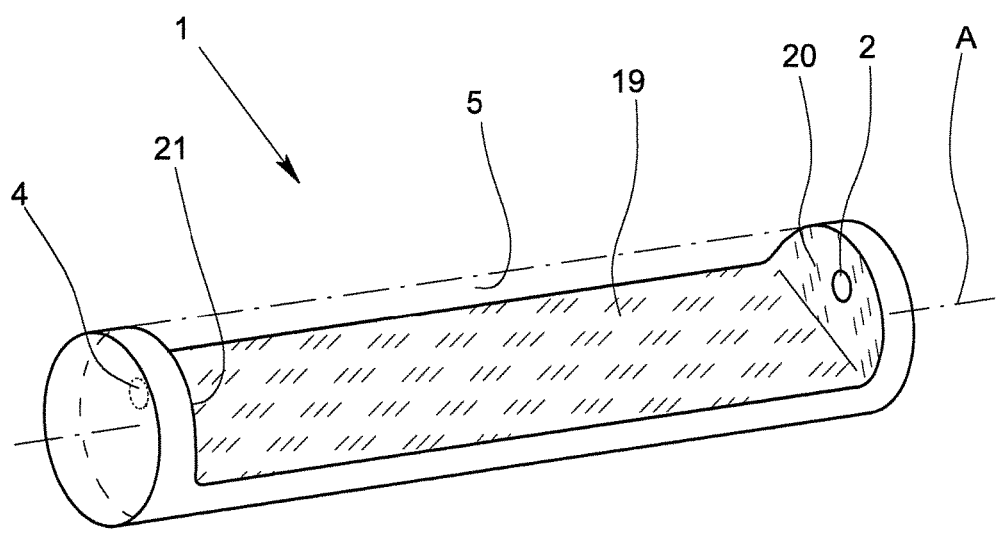
FIG. 2 is a perspective view of a second embodiment of a measuring rod according to the invention with a recess defining the measuring section of the measuring rod.

FIG. 2 shows a second embodiment of a measuring rod 1 according to the invention in a three-dimensional view, wherein the measuring rod 1 has a first sender unit 2 for transmission of a first acoustic or electromagnetic signal and a first receiver device 4 for receiving the first measuring signal, wherein the sender unit 2 and the receiver unit 4 define a measuring section and wherein the sender unit 2 and the receiver unit 4 are arranged in such a manner that the measuring signal crosses the measuring section and, at least during operation without flow, is received by the receiving unit 4. Furthermore, the measuring rod 1 has a recess 5 extending along the longitudinal axis A, wherein at least one first, flat longitudinal surface 19 and two end faces 20, 21 are formed by the recess 5 in the measuring rod and the measuring section is formed in the recess 5 between the two end faces 20, 21.

Such a design of the measuring section has the advantage that at least the flow to be verified is rectified in the area of the measuring section by the flat longitudinal surface 19, whereby the verification of a medium is simplified due to the interaction of the medium with the measuring signal.

As a result, FIG. 2 shows an embodiment of a measuring rod 1 that can be particularly flexibly used, also in tubes having a large nominal diameter and that has improved characteristics in respect to the verification of a quickly flowing medium.

Figure 3:
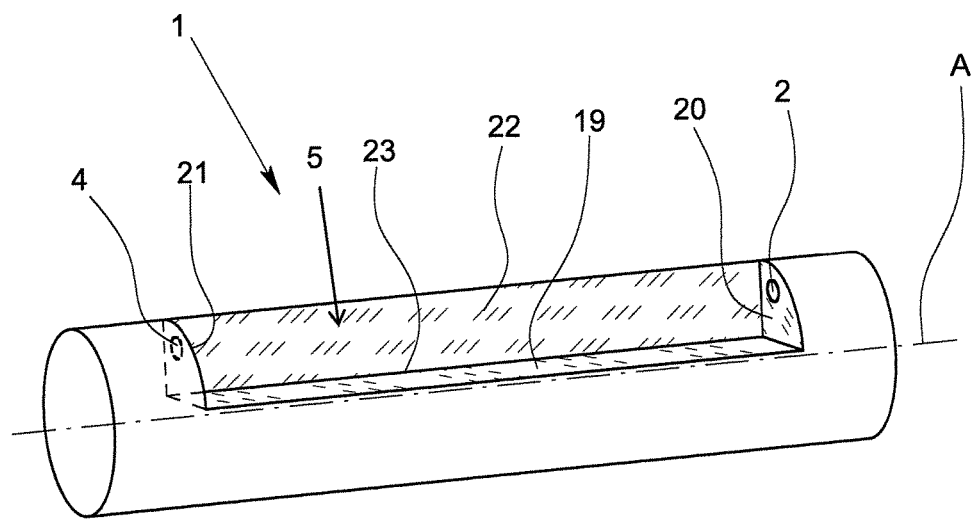
FIG. 3 is a perspective view of a third embodiment of a measuring rod according to the invention with a recess having an integrated vortex edge, the recess defining the measuring section of the measuring rod.

FIG. 3 shows a further, third embodiment of a measuring rod 1 according to the invention having a longitudinal axis A in a three-dimensional view. the measuring rod 1 comprises a first sender unit 2 and a first receiver unit 4, which define a measuring section, wherein the first sender unit 2 is arranged in such a manner that the first measuring signal crosses the measuring section and wherein the first receiver unit 4 is such that it, during operation without flow, receives the first measuring signal after crossing the measuring section. Furthermore, the measuring rod 1 has a recess 5 extending along its longitudinal axis A, wherein a first longitudinal surface 19 and two end faces 20, 21 are formed by the recess 5 in the measuring rod 1 and the measuring section is formed in the recess 5 between the two end faces 20, 21. Additionally, a second longitudinal surface 22 is formed by the recess 5, wherein the first longitudinal surface 19 and the second longitudinal surface 22 meet at a longitudinal edge 23 and form an angle.

During operation, the illustrated measuring rod 1 is preferably inserted into the flow cross section of a tube in such a manner that the second longitudinal surface 22 is arranged before the measuring section in respect to flow direction. Then, the second longitudinal surface 22 creates a vortex signature of the flowing medium within the measuring section, whereby the verification of the medium, as is also described in the scope of the following embodiments, is simplified.

Figure 4:
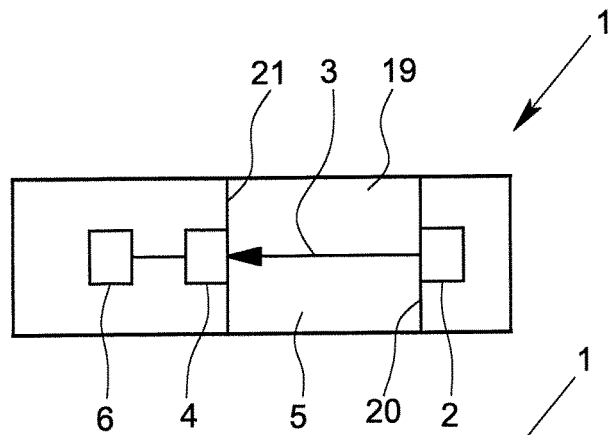
FIG. 4 is a schematic sectional view of a fourth embodiment of a measuring rod according to the invention with a recess.

FIG. 4 shows a sectional view of a fourth embodiment of a measuring rod 1 for the verification of a quickly flowing medium in a tube. The measuring rod 1 has a first sender unit 2 for transmission of a first acoustic or electromagnetic measuring signal 3 and a first receiver unit 4 for receiving the first measuring signal 3. The sender unit 2 and the receiver unit 4 are integrated in the measuring rod 1 in the shown embodiment. Additionally, the measuring rod 1 has a recess 5 extending along the longitudinal axis, wherein a first longitudinal surface 19 and two end faces 20, 21 are formed by the recess 5, and wherein a measuring section is formed in the recess 5 between the two end faces. During operation of the measuring rod, the medium to be verified flows through the measuring section. The first sender unit 2 is arranged in such a manner that the first measuring signal 3 crosses the measuring section and the first receiver signal 4 is arranged in such a manner that it, at least in operation without flow, receives the first measuring signal 3 after it crosses the measuring section.

Additionally, a first evaluation unit 6 is connected to the first receiver unit 4. If a quickly flowing medium is present within the measuring section, then the interaction of the measuring signal with the medium causes a measurable effect, which is detected by the receiver unit 4 and determined by the evaluation unit 6. For example, the interaction of a medium with an electromagnetic measuring signal 3 of the medium causes a phase shift depending on the permittivity of the medium and/or a damping of the amplitude. Alternatively, if the measuring signal 3 is designed as an acoustic signal, in particular as an ultrasound signal, the medium can be verified in that the receiver unit 4 receives an ultrasound signal during operation without flow, whereas, in the presence of a quickly flowing medium, the measuring signal 3 does not reach the receiver unit 4 due to the high speed of the medium, whereby the detected signal is interrupted.

As a result, FIG. 4 shows an advantageous embodiment of a measuring rod 1 that provides a reliable verification of a quickly flowing medium and that can be particularly easily inserted into tubes having different nominal diameters due to its design.

Figure 5:
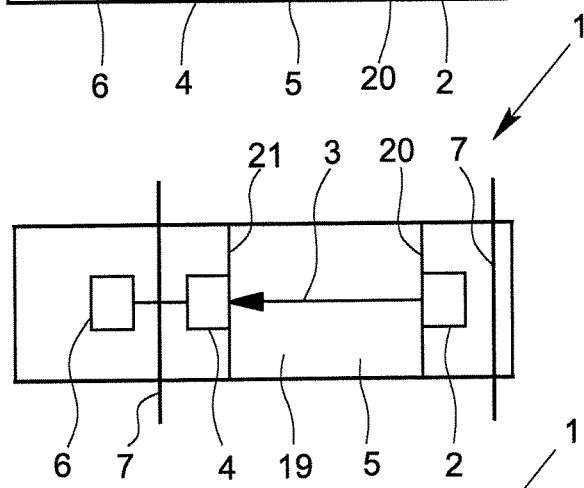
FIG. 5 is a schematic sectional view of a fifth embodiment of a measuring rod according to the invention with a recess and with flow rectifiers.

FIG. 5 shows a sectional view of a fifth embodiment of a measuring rod 1, comprising a first sender unit 2 for transmission of a first acoustic or electromagnetic measuring signal 3 and a first receiver unit 4 for receiving the first measuring signal, wherein the sender unit 2 and the receiver unit 4 are integrated in the measuring rod 1. A first longitudinal surface 19 and two end faces 20, 21 are formed by the recess 5, wherein the measuring section is formed in the recess between the two end faces 20, 21, the medium to be verified flowing through said measuring section during operation. Additionally, an evaluation unit 6 is provided, which is connected to the receiver unit 4 and which is also integrated in the measuring rod 1.

Furthermore, the illustrated measuring rod 1 has a flow rectifier in the form of two wing-shaped profile bodies 7, which are arranged in the area of the measuring section, so that they cause a rectified flow of the medium to be verified in the area of the measuring section during operation.

A rectified flow has the advantage that the effect verified due to the interaction of the medium with the measuring signal 3 is subject to fewer fluctuations caused by chance turbulences. The verification of a flowing medium takes place with particularly high reliability according to this embodiment.

Figure 6:
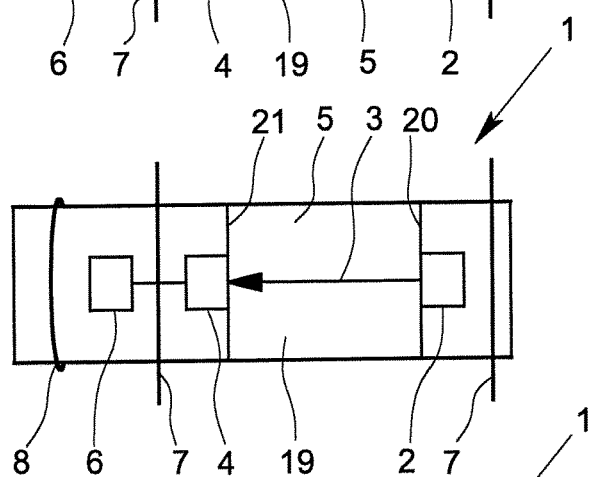
FIG. 6 is a schematic sectional view of a sixth embodiment of a measuring rod according to the invention with a protective ring.

A sectional view of a further, sixth embodiment of a measuring rod 1 is illustrated in FIG. 6, comprising a first sender unit 2 for transmission of a first acoustic or electromagnetic measuring signal 3 and a first receiver unit 4 for receiving the first measuring signal 3, wherein the sender unit 2 and the receiver unit 4 are integrated in the measuring rod 1. A first longitudinal surface 19 and two end faces 20, 21 are formed by a recess 5, wherein the measuring section is formed in the recess 5 between the two end faces 20, 21, the medium to be verified flowing through said measuring section during operation. Additionally, an evaluation unit 6 is provided, which is connected to the receiver unit 4 and which is also integrated in the measuring rod 1. Furthermore, wing-shaped profile bodies 7 are arranged in the area of the measuring section, which cause a rectified flow in the area of the measuring section during operation.

Additionally, the measuring rod 1 illustrated in FIG. 6 has a protective ring 8 arranged between the tube-side end and the measuring section of the measuring rod 1, wherein the protective ring 8 annularly encompasses the circumference of the measuring rod 1 and wherein the protective ring 8 prevents a transgression of liquid from the tube-side end of the measuring section. Such an embodiment is particularly advantageous when the measuring rod 1 is used for the verification of media, which at least partially have a liquid. During operation, the protective ring protects the measuring section from liquid running off on the inner wall of the tube.

Figure 7:
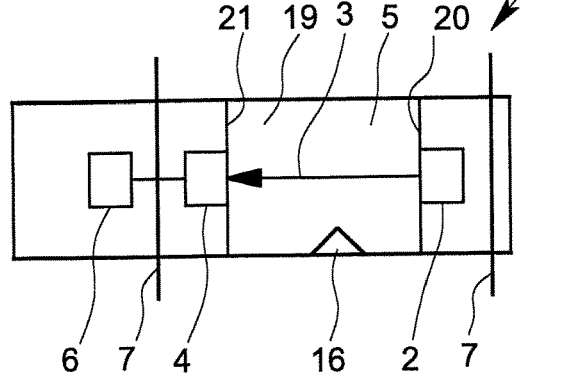
FIG. 7 is a schematic sectional view of a seventh embodiment of a measuring rod according to the invention with a bluff body.

A further, particularly advantageous embodiment of the measuring rod 1 according to the invention is shown in a sectional view in FIG. 7. As described above, the measuring rod 1 in FIG. 7 also has a first sender unit 2 for transmission of a first acoustic or electromagnetic measuring signal 3 and a first receiver unit 4 for receiving the first measuring signal 3, wherein the sender unit 2 and the receiver unit 4 are integrated in the measuring rod 1. The first longitudinal surface 19 and two end faces 20, 21 are formed by a recess 5, wherein the measuring section is formed in the recess 5 between the two end faces 20, 21, the medium to be verified flowing through said measuring section during operation. An evaluation unit 6 is also provided, which is connected to the receiver unit 4 and which is integrated in the measuring rod 1. Furthermore, wing-shaped profile bodies 7 are arranged in the area of the measuring section, which cause rectified flow of the medium in the area of the measuring section.

Additionally, the measuring rod illustrated in FIG. 7 has a bluff body 16, which is arranged before the measuring section in respect to flow direction. During operation, the medium to be verified forms vortices behind the bluff body within the measuring section, which can be detected by means of the measuring signal 3. Thereby, in particular the combination of the wing-shaped profile bodies 7 with the bluff body 16 create a vortex signature that can be detected with a particularly high reliability.

In a further embodiment, the bluff body 16 is an active bluff body, which is deflected by a respective activation, in particular is excited to oscillations, so that a certain vortex signature is specifically generated.

If the measuring signal 3 is an electromagnetic signal, for example a radar or microwave signal, the verification of the vortex signature is based on the effect that pressure fluctuations are present within the vortex, which affect the permittivity and, in this respect, for example, cause a phase change of the radar or microwave signals, which is detected by the receiver unit 4 and determined by the evaluation unit 6. Accordingly, the verifiable effect of interaction between the medium and the measuring signal is clearly intensified by the presence of the vortex signature. Thereby, the vortex signature emerges particularly clearly in the shown embodiment, since the bluff body 16 is arranged within the wing-shaped profile bodies 7, i.e., is located in the area of the rectified flow generated during operation. Additionally, the vortex signature can also be detected by means of acoustic ultrasound signals, since the pressure or speed fluctuations prevailing within the vortex change the phasing of the acoustic measuring signal, so that, as a result, a phase-modulated measuring signal is created.

Figure 8:
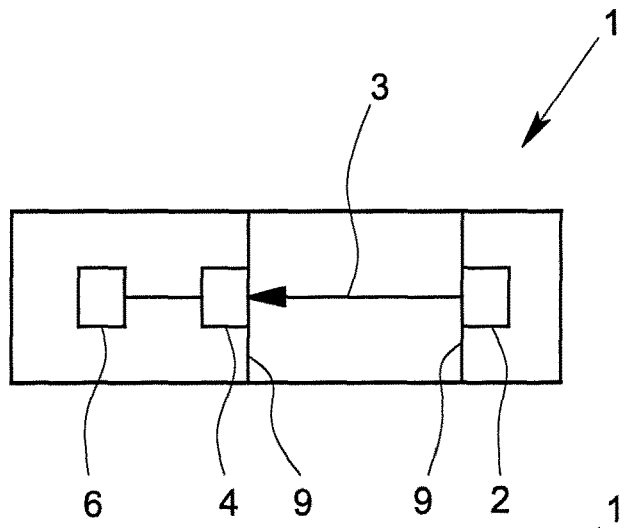
FIG. 8 is a schematic sectional view of an eighth embodiment of a measuring rod according to the invention.

FIG. 8 shows a sectional view of an eighth embodiment of a measuring rod 1 according to the invention having a first sender unit 2 for transmission of a first acoustic or electromagnetic measuring signal 3 and a first receiver unit 4 for receiving the first measuring signal 3, wherein the sender unit 2 and the receiver unit 4 are integrated in the measuring rod 1. Additionally, an evaluation unit 6 is provided that is connected to the receiver unit and that is also integrated in the measuring rod 1. A ceramic window 9 is arranged between the sender unit 2 and the recess 5 for coupling the measuring signal 3 into the measuring section. The coupling in of the measuring signal is carried out, in particular, with low loss. A ceramic window 9 is also arranged between the recess 5 and the receiver unit 4, whereby the measuring signal 3 can be particularly efficiently, i.e. low-loss, coupled out.

Figure 9:
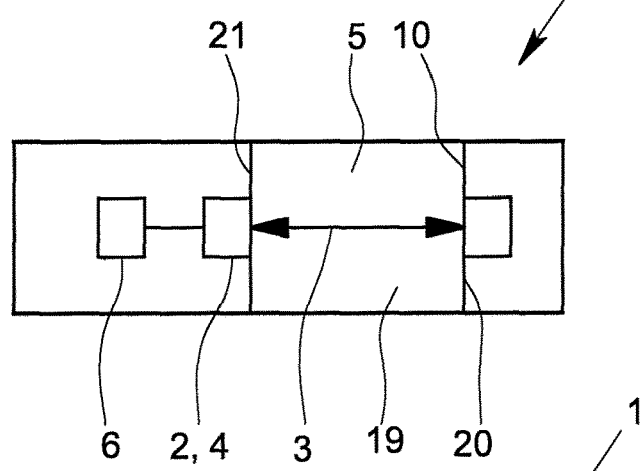
FIG. 9 is a schematic sectional view of a ninth embodiment of a measuring rod according to the invention with a reflector in the measuring section.

A ninth embodiment of a measuring rod 1 according to the invention is illustrated in FIG. 9, which has a first sender unit 2 for transmission of a first acoustic or electromagnetic measuring signal 3 and a first receiver unit 4 for receiving the first measuring signal 3, wherein the sender unit 2 and the receiver unit 4 are integrated in the measuring rod 1. A first longitudinal surface 19 and two end faces 20, 21 are formed by a recess 5, wherein the measuring section is formed in the recess 5 between the two end faces 20, 21, the medium to be verified flowing through said measuring section during operation. Additionally, an evaluation unit 6 is provided that is connected to the receiver unit 4 and is also integrated in the measuring rod 1. As opposed to the above embodiments, the sender unit 2 is designed in such a manner that it is simultaneously used as a receiver unit 4. A reflector 10 is arranged on the side of the measuring section opposite the sender unit 2, the reflector reflecting the first measuring signal 3 toward the receiver unit 4 during operation after it crosses the measuring section. This embodiment has the advantage that it is particularly simply designed. Furthermore, the effect of the interaction of the flowing medium with the measuring signal 3 is intensified due to the longer interaction section, so that a particularly reliable verification of the flowing medium is possible.

Figure 10:
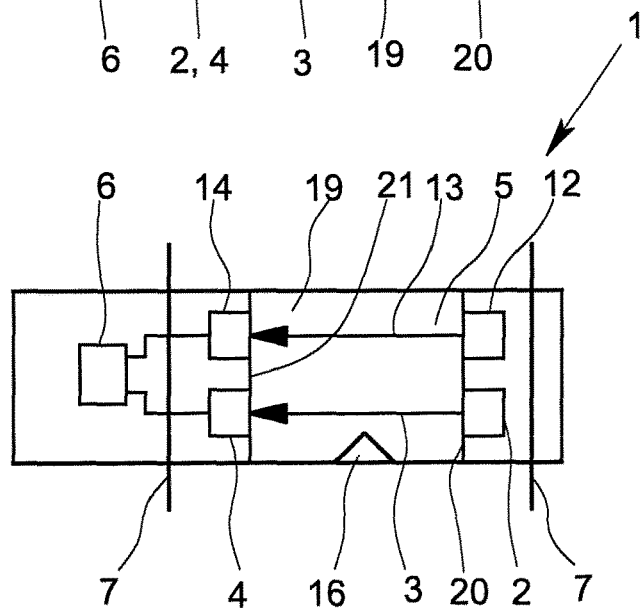
FIG. 10 is a schematic sectional view of a tenth embodiment of a measuring rod according to the invention with a double measuring section.

FIG. 10 shows a sectional view of a tenth embodiment of a measuring rod 1 comprising a first sender unit 2 for transmission of a first acoustic or electromagnetic measuring signal 3 and a receiver unit 4 for receiving the first measuring signal 3, wherein the sender unit 2 and the receiver unit 4 are integrated in the measuring rod 1. A first longitudinal surface 10 and two end faces 20, 21 are formed by a recess 5, wherein the measuring section is formed in the recess 5 between the two end faces 20, 21, the medium to be verified flowing through said measuring section during operation. Wing-shaped profile bodies 7 are arranged in the area of the measuring section and create a rectified flow in the area of the measuring section during operation. Additionally, the illustrated measuring rod 1 has a bluff body 16 that is arranged before the measuring section in respect to flow direction and, during operation, creates a vortex signature of the flowing medium in the area of the measuring section.

Furthermore, the illustrated measuring rod 1 has a second sender unit 12 and a second receiver unit 14, which are arranged behind the first sender unit 2 and behind the first receiver unit 4 in respect to flow direction. Additionally, an evaluation unit 6 is provided that is connected to the first receiver unit 4 and the second receiver unit 14 and is also integrated in the measuring rod 1. The vortex signature created by the bluff body 16 during operation passes through both the first measuring signal 3 as well as the second measuring signal 13. In addition to the verification of the presence of the flowing medium, information about its flow speed can also be obtained with the help of the cross correlation method, by means of which the measured measuring signals 3 and 13 are compared to one another in view of their agreement.

Consequently, this embodiment provides a measuring rod 1, with which a particularly exact and effective verification of a quickly flowing medium is possible.

Figure 11:
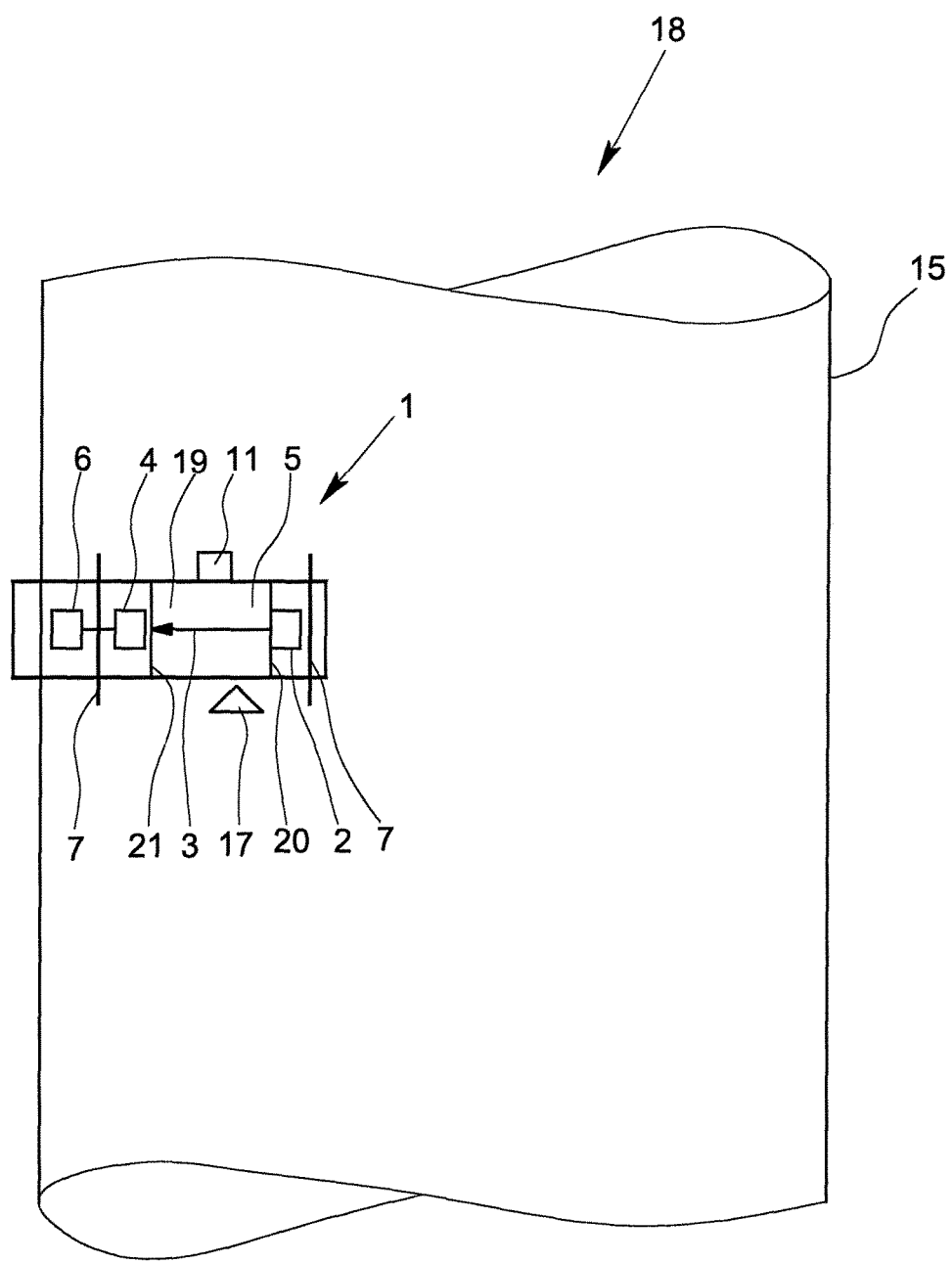
FIG. 11 is a schematic sectional view of a first embodiment of a measuring arrangement according to the invention.

FIG. 11 shows a sectional view of a first embodiment of a measuring arrangement 18 according to the invention. The measuring arrangement 18 comprises a tube 15 and one embodiment of a measuring rod 1 according to the invention, wherein the measuring rod 1 is arranged on the tube 15 in such a manner that the measuring rod 1 extends into the tube 15 at less than half the radius.

The measuring rod 1 has a first sender unit 2 for transmission of a first acoustic or electromagnetic measuring signal 3 and a first receiver unit 4 for receiving the first measuring signal 3, wherein the sender unit 2 and the receiver unit 4 are integrated in the measuring rod 1. A first longitudinal surface 19 and two end faces 20, 21 are formed by a recess 5, wherein the measuring section is formed in the recess 5 between the end faces 20, 21, the medium to be verified flowing through said measuring section during operation. Additionally, an evaluation unit 6 is provided that is connected to the receiver unit 4 and is also integrated in the measuring rod 1. Wing-shaped profile bodies 7 are arranged in the area of the measuring section and, during operation, create a rectified flow in the area of the measuring section.

A bluff body 16 is arranged before the measuring rod 1, which creates a vortex signature of the medium to be verified in the area of the measuring section during operation, whereby the verification of a quickly flowing medium can be clearly improved.

Furthermore, the measuring rod 1 has a pressure sensor 11, which is arranged behind the measuring section in respect to flow direction and which, during operation, detects the pressure fluctuations of the medium to be verified generated by the vortex signature.

As a result, the illustrated embodiment provides a measuring arrangement 18 that is particularly suitable for the verification of a quickly flowing medium.

What is claimed is:

1. A measuring rod with a longitudinal axis for insertion in a flow cross section of a tube and for verification of a flowing medium in the tube, comprising:
    at least one first sender unit for transmission of a first acoustic or electromagnetic measuring signal and
    at least one first receiver unit for receiving the first measuring signal,
    wherein the first sender unit and the first receiver unit define a measuring section,
    wherein the first sender unit is arranged in such a manner that the first measuring signal crosses the measuring section,
    wherein the first receiver unit is arranged in such a manner that, at least during operation without flow, the first receiver unit receives the first measuring signal after the first measuring signal crossing the measuring section, and
    wherein the measuring rod has a recess extending along its longitudinal axis, wherein at least one longitudinal surface and two end faces are formed in the measuring rod by the recess and the measuring section is formed in the recess between the two end faces.

2. The measuring rod (1) according to claim 1, wherein the first sender unit (2) and the first receiver unit (4) are arranged at a distance to one another in respect to the longitudinal axis (A).

3. The measuring rod (1) according to claim 1, wherein an electric contact of the first sender unit and the first receiver unit runs within the measuring rod.

4. The measuring rod (1) according claim 1, wherein that the sender unit and the receiver unit are located on a circumference of the measuring rod.

5. The measuring rod (1) according to claim 1, wherein a second longitudinal surface (22) is additionally formed by the recess (5) in the measuring rod (1), wherein the first longitudinal surface (19) and the second longitudinal surface (22) meet at a longitudinal edge (23) and comprise an angle.

6. The measuring rod (1) according to claim 1, wherein a third longitudinal surface is additionally formed by the recess in the measuring rod, and wherein the first longitudinal surface, the second longitudinal surface and the third longitudinal surface form a groove in the measuring rod.

7. The measuring rod (1) according to claim 1, wherein at least one flow rectifier is provided for generating a rectified flow of the medium to be verified in the area of the measuring section.

8. The measuring rod (1) according to claim 7, wherein the flow rectifier is formed of at least two wing-shaped profile bodies, and wherein the wing-shaped profile bodies are arranged at least in the area of the measuring section.

9. The measuring rod (1) according to claim 1, wherein at least one bluff body is provided, and wherein the bluff body is arranged before the measuring section in respect to a flow direction.

10. The measuring rod (1) according to claim 1, wherein at least one pressure sensor, is provided, and wherein the at least one pressure sensor is arranged within the measuring section or after it in respect to a flow direction.

11. The measuring rod (1) according to claim 1, wherein at least one protective ring is arranged between an end of the measuring rod and the measuring section, wherein the protective ring annularly encompasses the circumference of the measuring rod and wherein the protective ring prevents a transgression of liquid from the end of the measuring section.

12. The measuring rod (1) according to claim 1, wherein at least one ceramic window is arranged in an area of the recess for coupling at least the first measuring signal in and/or out.

13. The measuring rod according to claim 1, wherein at least one second sender unit is provided for transmission of a second acoustic or electromagnetic measuring signal and at least one second receiver unit is provided for receiving the second measuring signal, wherein the second sender unit is arranged in such a manner that the second measuring signal crosses the measuring section, wherein the second receiver unit is arranged in such a manner that, at least during operation without flow, the second receiver unit receives the second measuring signal after crossing the measuring section and wherein the second sender unit and the second receiver unit are arranged behind the first sender unit in respect to a flow direction and behind the first receiver unit in respect to the flow direction.

14. The measuring rod according to claim 1, wherein an evaluation unit is provided which is connected at least to the first receiver unit and wherein the evaluation unit is adapted to determine at least one of the amplitude, the phase, the intensity, the transit time of the measuring signal, and the cross correlation of the first and the second measuring signals.

15. A measuring arrangement, comprising:
a tube and
a measuring rod
wherein the measuring rod is arranged at least partially within the tube and comprises:
at least one first sender unit for transmission of a first acoustic or electromagnetic measuring signal and
at least one first receiver unit for receiving the first measuring signal,
wherein the first sender unit and the first receiver unit define a measuring section,
wherein the first sender unit is arranged in such a manner that the first measuring signal crosses the measuring section,
wherein the first receiver unit is arranged in such a manner that, at least during operation without flow, the first receiver unit receives the first measuring signal after the first measuring signal crossing the measuring section,
wherein the first receiver unit is positioned to receive the first measuring signal after the first measuring signal crossing the measuring section, and
wherein the measuring rod has a recess extending along its longitudinal axis, wherein at least one longitudinal surface and two end faces are formed in the measuring rod by the recess and the measuring section is formed in the recess between the two end faces.

16. The Measuring arrangement according to claim 15, wherein the tube has a radius and the measuring rod extends into the tube no more than half of the radius.

17. Measuring arrangement according to claim 15, wherein a bluff body is provided, wherein the bluff body is arranged before the measuring rod in a flow direction.

* * * * *